(12) United States Patent
Andreas et al.

(10) Patent No.: US 7,147,656 B2
(45) Date of Patent: Dec. 12, 2006

(54) APPARATUS AND METHODS FOR DELIVERY OF BRAIDED PROSTHESES

(75) Inventors: Bernard Andreas, Redwood City, CA (US); Ron French, Santa Clara, CA (US); Mark E. Deem, Mountain View, CA (US); Hanson S. Gifford, III, Woodside, CA (US)

(73) Assignee: Xtent, Inc., Menlo Park, CA (US)

( * ) Notice: Subject to any disclaimer, the term of this patent is extended or adjusted under 35 U.S.C. 154(b) by 493 days.

(21) Appl. No.: 10/306,620

(22) Filed: Nov. 27, 2002

(65) Prior Publication Data

US 2003/0135258 A1 Jul. 17, 2003

Related U.S. Application Data

(60) Provisional application No. 60/336,607, filed on Dec. 3, 2001.

(51) Int. Cl.
*A61F 2/06* (2006.01)
(52) U.S. Cl. ...................................... 623/1.11
(58) Field of Classification Search ...... 623/1.11–1.15, 623/1.23; 604/508
See application file for complete search history.

(56) References Cited

U.S. PATENT DOCUMENTS

| | | | |
|---|---|---|---|
| 4,564,014 A | 1/1986 | Fogarty et al. | |
| 4,681,110 A * | 7/1987 | Wiktor | 606/194 |
| 4,733,665 A | 3/1988 | Palmaz | |
| 4,739,762 A | 4/1988 | Palmaz | |
| 4,775,337 A | 10/1988 | Van Wagener et al. | |
| 4,886,062 A | 12/1989 | Wiktor | |
| 4,994,066 A | 2/1991 | Voss | |
| 4,994,069 A | 2/1991 | Ritchart et al. | |
| 5,092,877 A | 3/1992 | Pinchuk | |
| 5,102,417 A | 4/1992 | Palmaz | |
| 5,195,984 A | 3/1993 | Schatz | |
| 5,217,495 A * | 6/1993 | Kaplan et al. | 623/13.18 |
| 5,226,913 A | 7/1993 | Pinchuk | |
| 5,246,421 A | 9/1993 | Saab | |
| 5,421,955 A | 6/1995 | Lau et al. | |
| 5,514,093 A | 5/1996 | Ellis et al. | |
| 5,514,154 A | 5/1996 | Lau et al. | |
| 5,527,354 A | 6/1996 | Fontaine et al. | |
| 5,549,551 A | 8/1996 | Peacock, III et al. | |
| 5,562,725 A * | 10/1996 | Schmitt et al. | 623/1.53 |
| 5,571,086 A | 11/1996 | Kaplan et al. | |
| 5,607,463 A | 3/1997 | Schwartz et al. | |
| 5,628,775 A | 5/1997 | Jackson et al. | |
| 5,634,928 A | 6/1997 | Fischell et al. | |
| 5,676,654 A | 10/1997 | Ellis et al. | |
| 5,697,948 A | 12/1997 | Marin et al. | |

(Continued)

FOREIGN PATENT DOCUMENTS

WO  WO 00/15151 A1  3/2000

(Continued)

*Primary Examiner*—Suzette J-J Gherbi
(74) *Attorney, Agent, or Firm*—Townsend and Townsend and Crew LLP

(57) ABSTRACT

Blood vessels and other body lumens are expanded using an evertible braided prosthesis. The braided prosthesis is delivered to the blood vessel in a radially collapsed configuration. A leading edge of the braided prosthesis is then everted so that it expands as it is advanced through the blood vessel. Optionally, the prosthesis can be provided with a biologically active substance in order to inhibit hyperplasia or have other desired biological effects.

21 Claims, 2 Drawing Sheets

U.S. PATENT DOCUMENTS

| | | | |
|---|---|---|---|
| 5,722,669 A | 3/1998 | Shimizu et al. | |
| 5,735,869 A | 4/1998 | Fernandez-Aceytuno | |
| 5,749,848 A | 5/1998 | Jang et al. | |
| 5,755,772 A | 5/1998 | Evans et al. | |
| 5,769,882 A | 6/1998 | Fogarty et al. | |
| 5,772,669 A | 6/1998 | Vrba | |
| 5,776,141 A | 7/1998 | Klein et al. | |
| 5,807,398 A | 9/1998 | Shaknovich | |
| 5,833,694 A | 11/1998 | Poncet | |
| 5,836,964 A | 11/1998 | Richter et al. | |
| 5,843,092 A | 12/1998 | Heller et al. | |
| 5,858,556 A | 1/1999 | Eckert et al. | |
| 5,891,190 A | 4/1999 | Boneau | |
| 5,895,398 A | 4/1999 | Wensel et al. | |
| 5,902,332 A | 5/1999 | Mickley et al. | |
| 5,961,536 A | 10/1999 | Foreman et al. | |
| 5,980,552 A | 11/1999 | Pinchasik | |
| 6,022,359 A | 2/2000 | Frantzen | |
| 6,066,155 A | 5/2000 | Amann et al. | |
| 6,090,063 A | 7/2000 | Makower et al. | |
| 6,090,136 A | 7/2000 | McDonald et al. | |
| 6,143,016 A | 11/2000 | Bleam et al. | |
| 6,187,034 B1 | 2/2001 | Frantzen | |
| 6,190,402 B1 | 2/2001 | Horton et al. | |
| 6,241,691 B1 | 6/2001 | Ferrera et al. | |
| 6,251,134 B1 | 6/2001 | Alt et al. | |
| 6,254,628 B1 * | 7/2001 | Wallace et al. | 623/1.12 |
| 6,258,117 B1 | 7/2001 | Camrud et al. | |
| 6,315,794 B1 | 11/2001 | Richter | |
| 6,357,104 B1 * | 3/2002 | Myers | 29/527.1 |
| 6,383,171 B1 * | 5/2002 | Gifford et al. | 604/508 |
| 6,419,693 B1 | 7/2002 | Fariabi | |
| 6,451,025 B1 | 9/2002 | Jervis | |
| 6,451,050 B1 | 9/2002 | Rudakov et al. | |
| 6,468,299 B1 | 10/2002 | Stack et al. | |
| 6,485,510 B1 | 11/2002 | Camrud et al. | |
| 6,511,468 B1 | 1/2003 | Cragg et al. | |
| 6,520,987 B1 | 2/2003 | Plante | |
| 2001/0044595 A1 * | 11/2001 | Reydel et al. | 604/98.02 |
| 2002/0138132 A1 | 9/2002 | Brown | |
| 2002/0156496 A1 | 10/2002 | Chermoni | |
| 2003/0114922 A1 * | 6/2003 | Iwasaka et al. | 623/1.16 |
| 2003/0176909 A1 * | 9/2003 | Kusleika | 623/1.11 |

FOREIGN PATENT DOCUMENTS

| | | |
|---|---|---|
| WO | WO 00/32136 A1 | 6/2000 |
| WO | WO 03/022178 A1 | 3/2003 |

* cited by examiner

APPARATUS AND METHODS FOR DELIVERY OF BRAIDED PROSTHESES

CROSS-REFERENCES TO RELATED APPLICATIONS

The present application is a non-provisional of U.S. patent application Ser. No. 60/336,607, filed Dec. 3, 2001, the full disclosure of which is incorporated herein by reference.

BACKGROUND OF THE INVENTION

1. Field of the Invention.

The present invention relates generally to medical devices and methods. More particularly, the present invention relates to apparatus and methods for delivering braided and other everting prostheses within a body lumen, such as a blood vessel.

Coronary artery disease is the leading cause of death and morbidity in the United States and Western society. In particular, atherosclerosis in the coronary arteries can cause myocardial infarction, commonly referred to as a heart attack, which can be immediately fatal or even if survived, cause damage to the heart which can incapacitate the patient.

While coronary artery bypass surgery can be an effective treatment for stenosed arteries resulting from atherosclerosis or other causes, it is a highly invasive, costly procedure, which typically requires substantial hospital and recovery time. Percutaneous transluminal coronary angioplasty, commonly referred to as balloon angioplasty, is less invasive, less traumatic, and significantly less expensive than bypass surgery. Heretofore, however, balloon angioplasty has not been considered as effective a treatment as bypass surgery. The effectiveness of balloon angioplasty, however, has improved significantly with the introduction of stenting, which involves the placement of a scaffold structure within the artery which has been treated by balloon angioplasty. The stent inhibits abrupt reclosure of the artery and has some benefit in inhibiting subsequent restenosis resulting from hyperplasia. Recently, experimental trials have demonstrated that coating stents with anti-proliferative drugs, such as paclitaxel, can significantly reduce the occurrence of hyperplasia in angioplasty treated coronary arteries which have been stented with the coated stents.

While the combination of balloon angioplasty with drug-coated stents holds great promise, significant challenges still remain. Of particular interest to the present invention, the treatment of extended or disseminated disease within an artery remains problematic. Most stents have a fixed length, typically in the range from 10 mm to 30 mm, and the placement of multiple stents to treat disease over a longer length requires the successive use of multiple balloon stent delivery catheters. Moreover, it can be difficult to stent an angioplasty-treated region of a blood vessel with the optimum stent length.

For these reasons, it would be desirable to provide improved stents, stent delivery systems, stenting methods, and the like, for the treatment of patients having coronary artery disease, as well as other occlusive diseases of the vasculature and other body lumens. In particular, it would be desirable to provide stents, delivery systems, and methods for the treatment of disseminated and variable length stenotic regions within the vasculature. For example, it would be desirable to provide a practical method which permits a physician to deliver extended lengths of braided prostheses to blood vessels and other body lumens. At least some of these objectives will be met by the inventions described hereinafter.

2. Description of the Background Art.

U.S. Pat. No. 5,755,772 describes a tubular prosthesis and method for its implantation by positioning the prosthesis at a target site, and everting an end session to lock the stent after expansion has been completed; and U.S. Pat. No. 5,769,882 describes conformable tubular prostheses and their placement in blood vessels.

BRIEF SUMMARY OF THE INVENTION

The present invention provides methods and apparatus for the stenting of body lumens, typically blood vessels, and more typically coronary arteries. The methods and systems will also find significant use in the peripheral vasculature, the cerebral vasculature, and in other ducts, such as the biliary duct, the fallopian tubes, and the like. The terms "stent" and "stenting" are defined to include any of the wide variety of expandable scaffolds which are designed to be intraluminally introduced to a treatment site and expanded in situ to apply a radially outward force against the inner wall of the body lumen at that site. Stents commonly comprise an open lattice structure, typically formed from a malleable or elastic metal.

The stents of the present invention will comprise evertible structures which radially expand upon eversion to assume a non-collapsible diameter which remains in place within the body lumen to support the luminal wall. Typically, the evertible stent structures will comprise braided structures, but other structures, such as counterwound helices, will also be capable of eversion. In some instances, laser cut helical and other patterned metal tubes, particularly those formed from nickel titanium and other shape memory alloys, may be used. Thin wall tubes formed from polymeric materials, such as polyethylene terephthalate (PET), expanded polytetrafluoroethyolene (e PTFE), may also find use, even without patterning.

The braided and other evertible stent structures of the present invention may be formed from metals, including both malleable metals and elastic metals, such as shape memory metals, as well as from polymeric materials. Usually, the braided structures will comprise individual ribbons of the desired material which are interwoven to form a braid so that the braid may be axially elongated to assume a narrow diameter configuration and thereafter be everted to assume a larger diameter configuration. By "evert" it is meant that a leading edge of the prosthesis is turned outwardly and backwardly relative to the narrow diameter portion thereof. In the preferred methods and apparatus of the present invention, as described in more detail below, such eversion will be achieved by initially holding the prosthesis in its narrow diameter configuration with the leading portion everted and fixed to an outer portion of a catheter. This leading portion is referred to as the "fixed end." The remainder of the prosthesis which remains in its narrow diameter configuration is held within a passage or lumen of a delivery catheter, and means are provided for pushing the "advancable end" of the prosthesis which is in the lumen forwardly relative to the fixed end. In this way, the leading edge of the prosthesis moves forward continuously relative to the fixed end as it everts radially outwardly.

The use of such braided and other evertible prostheses provides a number of advantages. For example, the braided structure is highly flexible, particularly in its narrow diameter configuration, allowing the introduction of relatively long stent segments without significantly limiting the ability of the delivery catheter to pass through torturous regions of the vasculature or other body lumens. Additionally, by everting the prosthesis so that its outer portion remains stationary relative to the fixed end (and thus also relative to the delivery catheter), the stent will be able to pass through relatively small body lumens since it advances much like a tractor tread in moving forwardly through the lumen. In the case of vascular treatments, the stents of the present invention will usually be used following other primary interventions, such as angioplasty, atherectomy, aneurysm repair, or the like. It will be possible, however, in certain instances, to deliver the stent without prior intervention because of the ability to advance through tight lesions and to dilate the lesion as it passes therethrough.

Usually, the methods and apparatus of the present invention will be used to deliver a single stent having a predetermined length. In other instances, however, it will be possible to provide a means for severing the stent on the catheter itself In such cases, the methods and apparatus of the present invention will be capable of delivering variable lengths of stent depending on the nature and extent of the disease being treated. That is, the apparatus will be used to deliver the stent under fluoroscopic or other observation, and after a desired length of stent has been deployed, the deployed length can be severed from the length which remains carried within the delivery catheter.

In a first aspect, methods according to the present invention thus comprise positioning a tubular prosthesis at a target site within a body lumen. The prosthesis is then everted so that an inside surface is exposed radially outwardly and advanced over a length of the wall of the body lumen. Usually, positioning comprises introducing a delivery catheter having a passage which carries the tubular prosthesis at least partly in a radially collapsed configuration. Everting usually comprises pushing the tubular prosthesis from the catheter so that a leading portion of the prosthesis everts and radially expands as it exits the catheter or passage. This is usually accomplished by forwardly advancing a portion of the catheter to push the prosthesis from the catheter. In a preferred aspect of the present invention, an advancable segment of the prosthesis is carried in the passage in the radially collapsed configuration. A fixed end of the prosthesis is held stationary relative to the catheter in a partially everted configuration. Everting then comprises pushing a proximal end (i.e., an end or portion of the prosthesis which is radially collapsed within the delivery catheter) to cause a middle portion of the prosthesis to progressively evert and advance distally relative to the fixed end. In the case of braided prostheses, the braided structure will shorten as the radius expands so that the "advancable" proximal end prosthesis is pushed forward at a rate which is faster than the rate at which the everted prosthesis covers the wall of the body lumen. In preferred embodiments, the prosthesis releases an active substance which inhibits hyperplasia after the prosthesis has been placed in the body lumen.

In a second aspect of the present invention, apparatus for delivering a prosthesis to a body lumen comprise a catheter having a passage. A tubular prosthesis is carried at least partially in the passage in a radially collapsed configuration. A mechanism for advancing the prosthesis from the passage so that the prosthesis everts and radially expands as it is advanced is also provided. The tubular prosthesis is preferably a braided tube, and the braided tube is composed at least partly from a material selected from the group consisting of stainless steel, shape memory alloys, and polymer resins. Optionally, the prosthesis may carry a source of an active substance, such as a substance which inhibits hyperplasia. Exemplary active substances include anti-neoplastic drugs such as paclitaxel, methotrexate, and batimastal; antibiotics such as doxycycline, tetracycline, rapamycin, and actinomycin; immunosuppressant such as dexamethosone, methyl prednisolone, nitric oxide sources such as nitroprussides; estrogen; estradiols; and the like. Such active substances may be carried on the prosthesis in a variety of ways. For example, they may be coated by spraying, dipping, painting, or the like. Alternatively, they may be stored in reservoirs, i.e., etched depressions or spaces within the prosthesis structure. In the latter case, delivery is often controlled using a microporous, macroporous, or diffusible rate-controlling membrane. In other instances, the active substances may be incorporated in porous or nonporous polymeric layers which are incorporated over or within the braided or other evertible stent structures.

In the exemplary apparatus of the present invention, the fixed end of the prosthesis is everted over an outside surface of the catheter. An advancable end of the prosthesis remains in the catheter passage. A pusher to push the middle of the prosthesis distally relative to the catheter to evert and advance a leading edge of the prosthesis relative to the fixed end is also provided. Optionally, a central tube is disposed inside of the collapsed portion of the prosthesis, and further optionally, the central tube may be advancable together with the pusher to evert the prosthesis.

DETAILED DESCRIPTION OF THE INVENTION

Figure 1:
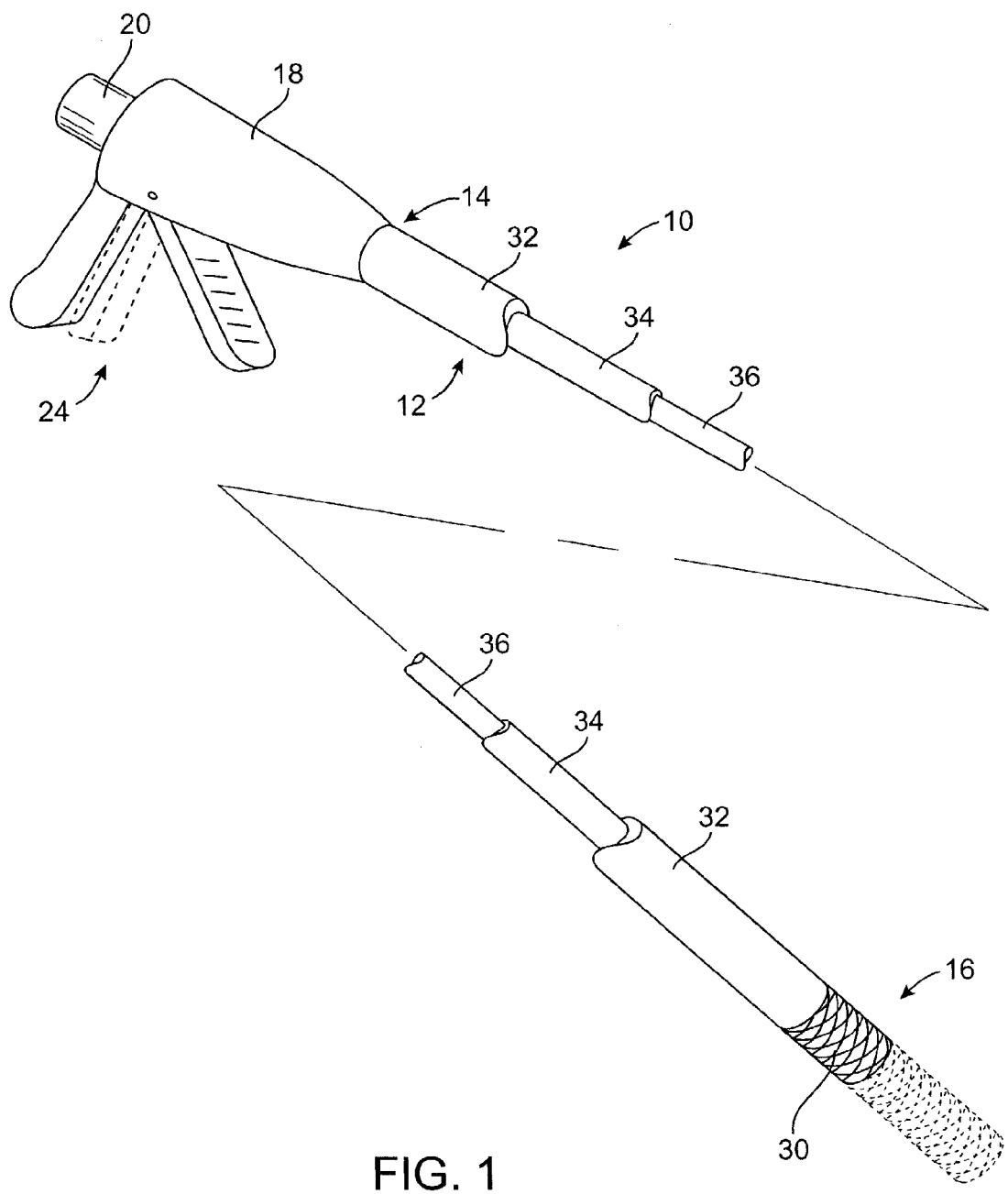
FIG. 1 is a perspective view illustrating a stent delivery catheter constructed in accordance with the principles of the present invention.

Referring now to FIG. 1, the stent delivery catheter 10 comprises a catheter body 12 having a proximal end 14 and a distal end 16. The catheter body 12 is formed from a conventional catheter material, such as a natural or synthetic polymer, such as silicone rubber, polyethylene, polyvinylchloride, polyurethane, polyester, polytetrafluoroethylene, nylon, and the like. The body may be formed as a composite having one or more reinforcement layers incorporated within a polymeric shell in order to enhance strength, flexibility, and toughness. For intravascular use, the catheter body will typically have a length in the range from 40 cm to 150 cm, usually being between 40 cm and 120 cm for peripheral blood vessels and between 110 cm and 150 cm for coronary arteries. The outer diameter of the catheter body may vary depending on the intended use, typically being between 3 French and 15 French, usually from 5 French to 9 French (one French=0.33 mm).

Catheter 10 further comprises a handle 18 at its proximal end 14. The handle has a guidewire port 20 at its distal end as well as a handle grip 24 which is actuable to extend and release evertible prosthesis 30 from the distal end 16. The catheter body 12 comprises an outer tube 32, a middle tube 34 which coaxially and slidably mounted within a lumen of the outer tube 32, and an inner tube 36 which is slidably and coaxially mounted within a lumen of the middle tube 34. Inner tube 36 has a central lumen for receiving a guidewire, as described in detail below.

Figure 2A:
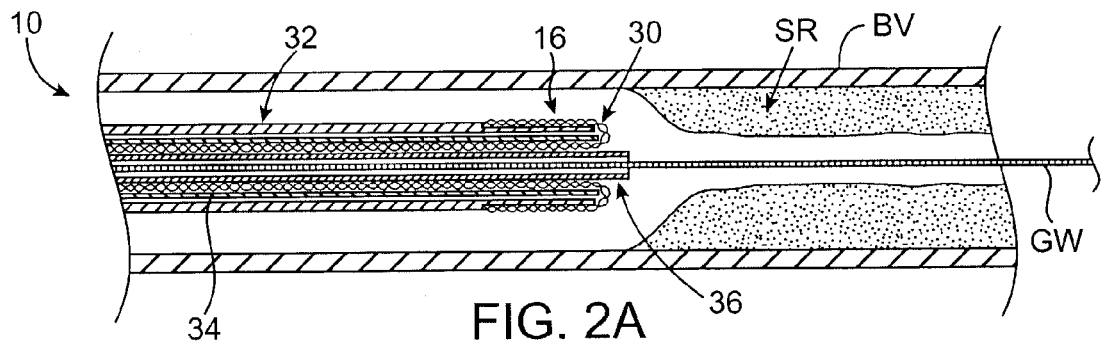
FIGS. 2A–2D illustrate use of the catheter in FIG. 1 for deploying a braided stent within a stenosed region in a blood vessel.

Referring now to FIGS. 2A–2D, delivery of the prosthesis 30 within a stenosed region SR of a blood vessel BV is described. The distal end 16 of the catheter 10 is introduced over a guidewire GW to the stenosed region SR as shown in FIG. 2A.

Figure 2B:
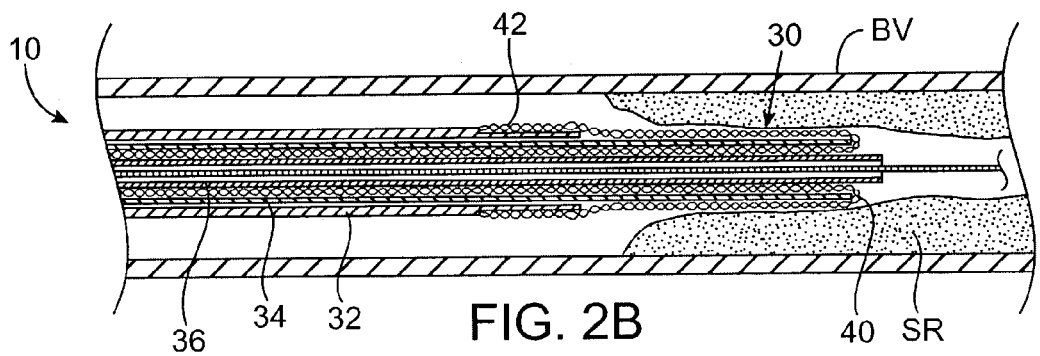

At that point, the prosthesis 30 is advanced forwardly or distally into the stenosed region SR of the blood vessel BV, as shown in FIG. 2B. In particular, both the inner tube 36 and the middle tube 34 are advanced forwardly or distally relative to the outer tube 32. This causes the leading edge 40 of the prosthesis 30 to advance into the stenosed region SR, engaging and partially dilating the lumen wall within this region.

Figure 2C:
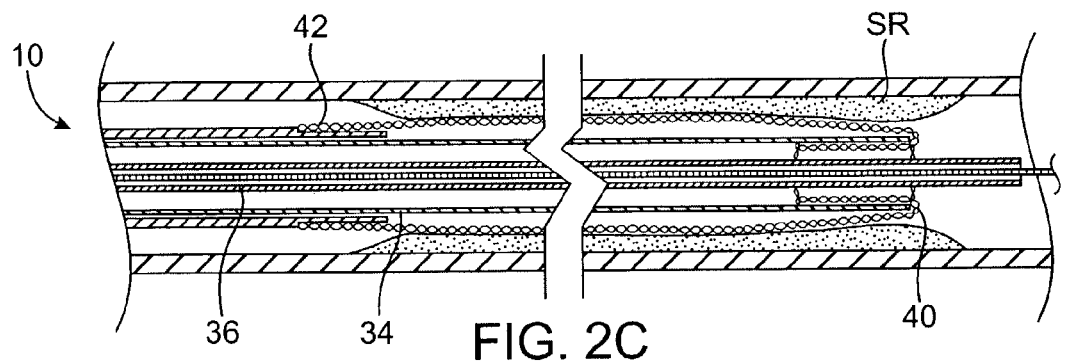

As the inner tube 36 and middle tube 34 are further advanced, as shown in FIG. 2C, the leading edge 40 of the prosthesis advances out through the other end of the stenosed region SR. During this entire deployment, fixed end 42 of the prosthesis has remained on the distal end of the outer tube 32 of the delivery catheter 10.

Figure 2D:
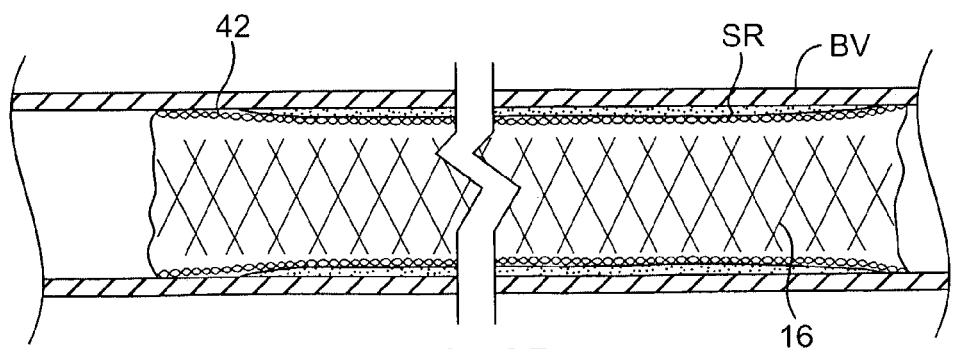

Once the prosthesis 30 is fully deployed, the outer tube 32 would be disengaged from the fixed end 42 of the prosthesis, e.g., by rotating or otherwise separating the catheter from the prosthesis, leaving the prosthesis 30 in place, as shown in FIG. 2D. As can be seen in FIG. 2D, the deployment of the prosthesis 30 has dilated the stenotic region. At this point, if the dilation is insufficient, or further anchoring of the prosthesis 30 is desired, a balloon or other expandable member may be expanded within the prosthesis 30 in a conventional manner. In one embodiment, for example, a balloon may be coupled with the outer tube 32 in such a way as to allow the balloon to be inflated to further anchor the prosthesis 30 in place.

It will be appreciated that the lengths, pitches, adjacent spacings, and the like, of the braided and other elements deployed according to the methods of the present invention can be controlled at the discretion of the treating physician. Thus, the methods and apparatus of the present invention provide useful flexibility for the treating physician to treat extended and disseminated disease in the vasculature and other body lumens.

Although the foregoing invention has been described in some detail by way of illustration and example, for purposes of clarity of understanding, it will be obvious that certain changes and modifications may be practices within the scope of the appended claims.

What is claimed is:

1. A method for delivering a prosthesis to a body lumen, said method comprising:
   positioning a tubular prosthesis at a target site within the body lumen; and
   everting the tubular prosthesis so that an inside surface is exposed radially outwardly and advanced over a length of a wail of the body lumen;
   wherein the prosthesis releases an active substance which inhibits hyperplasia after the prosthesis has been placed in the body lumen.

2. A method as in claim 1, wherein positioning comprises introducing a catheter having a passage which carries the tubular prosthesis at least partly in a radially collapsed configuration.

3. A method as in claim 1, wherein everting comprises pushing the tubular prosthesis from the catheter so that a leading portion of the prosthesis everts and radially expands as it exits the passage.

4. A method as in claim 3, wherein at least a portion of the catheter is advanced forwardly within the prosthesis as the prosthesis is pushed from the catheter.

5. A method as in claim 4, wherein an advancable segment of the prosthesis is carried in the passage in the radially collapsed configuration and a fixed end of the prosthesis is held stationary relative to the catheter in a partially averted configuration, wherein evening comprises pushing a proximal end of the advanceable segment to cause a middle portion to progressively evert and advance distally relative to the fixed end.

6. A method as in any one of claims 1–5, wherein the body lumen is a blood vessel.

7. A method as in any one of claims 1–5, wherein the tubular prosthesis comprises a braided structure.

8. A method as in claim 7, wherein the braided structure shortens as the radius expands so that the prosthesis must be advanced at a rate which is faster than the rate at which the everted prosthesis covers the wall of the body lumen.

9. A method as in claim 1, further comprising expanding the tubular prosthesis, using a balloon.

10. A method as in claim 1, further comprising severing a portion of the tubular prosthesis to allow the portion to remain in the body lumen.

11. Apparatus for delivering a prosthesis to a body lumen, said apparatus comprising:
    a catheter having a passage;
    a tubular prosthesis carried in the passage at least partially in a radially collapsed configuration; and
    a slidable member capable advancing the prosthesis from the passage so that said prosthesis is capable of everting and radially expands as it is advanced;
    wherein the prosthesis carries a source of an active substance.

12. Apparatus as in claim 11 wherein the tubular prosthesis comprises a braided tube.

13. Apparatus as in claim 12 wherein the braided tube is composed at least partly from a material selected from the group consisting of stainless steel, shape memory alloys, and polymer resins.

14. Apparatus as in claim 11 wherein the prosthesis is at least partially coated with the active substance.

15. Apparatus as in claim 11 wherein the prosthesis has at least one reservoir that carries the active substance.

16. Apparatus as in claim 11 wherein the prosthesis includes a polymeric layer, wherein said polymeric layer is loaded with the active substance.

17. Apparatus as in any one of claims 11–13 wherein a fixed end of the prosthesis is evened over an outside surface of the catheter and an advanceable end remaining in the passage, further comprising a pusher to push the middle of the prosthesis distally to evert and advance a leading edge of the prosthesis relative to the fixed end.

18. Apparatus as in claim 17 further comprising a central tube which is disposed inside of the collapsed portion of the prosthesis.

19. Apparatus as in claim 18 wherein the central tube is advanceable together wit the pusher to even the prosthesis.

20. Apparatus as in claim 17 further comprising an expandable balloon coupled with the outside surface of the catheter for expanding the prosthesis.

21. Apparatus as in claim 17 further comprising severing means for severing a portion of the prosthesis to allow the portion to remain in the body lumen.

* * * * *

UNITED STATES PATENT AND TRADEMARK OFFICE
CERTIFICATE OF CORRECTION

PATENT NO. : 7,147,656 B2 Page 1 of 1
APPLICATION NO. : 10/306620
DATED : December 12, 2006
INVENTOR(S) : Bernard Andreas et al.

It is certified that error appears in the above-identified patent and that said Letters Patent is hereby corrected as shown below:

On the Title Sheet:

Item (75) should read as follows:

(75) Inventors: Bernard Andreas, Redwood City, CA (US); Ron French, Santa Clara, CA (US); Mark E. Deem, Mountain View, CA (US); Hanson S. Gifford, III, Woodside, CA (US): Allan Will, Atherton, CA (US)

Signed and Sealed this

Twenty-ninth Day of May, 2007

JON W. DUDAS
*Director of the United States Patent and Trademark Office*